US012210008B2

(12) United States Patent
Brewer

(10) Patent No.: US 12,210,008 B2
(45) Date of Patent: Jan. 28, 2025

(54) FLEXIBLE WAFER TOTAL DISSOLVED SOLIDS PROBE AND METHODS OF USE THEREOF

(71) Applicant: Pentair Residential Filtration, LLC, Brookfield, WI (US)

(72) Inventor: Blake Brewer, Hanover Park, IL (US)

(73) Assignee: Pentair Residential Filtration, LLC, Brookfield, WI (US)

( * ) Notice: Subject to any disclaimer, the term of this patent is extended or adjusted under 35 U.S.C. 154(b) by 0 days.

(21) Appl. No.: 17/657,916

(22) Filed: Apr. 4, 2022

(65) Prior Publication Data

US 2022/0317106 A1   Oct. 6, 2022

Related U.S. Application Data

(60) Provisional application No. 63/200,951, filed on Apr. 5, 2021.

(51) Int. Cl.
| G01N 33/18 | (2006.01) |
| G01K 7/22 | (2006.01) |
| G01N 27/07 | (2006.01) |

(52) U.S. Cl.
CPC .......... *G01N 33/1886* (2013.01); *G01K 7/22* (2013.01); *G01N 27/07* (2013.01)

(58) Field of Classification Search
CPC ....... G01N 33/1886; G01N 27/07; G01K 7/22
USPC ....................................... 73/61.71
See application file for complete search history.

(56) References Cited

U.S. PATENT DOCUMENTS

| 7,759,948 B2 | 7/2010 | Tischendorf et al. |
| 2002/0105346 A1* | 8/2002 | Banks .................. G01N 17/02 324/700 |
| 2009/0246083 A1* | 10/2009 | Samborn ............... G01N 27/06 368/10 |

(Continued)

FOREIGN PATENT DOCUMENTS

| CA | 2627610 A1 * | 5/2007 | ......... G01N 33/1886 |
| CN | 108398195 A * | 8/2018 | |
| CN | 112129816 A * | 12/2020 | ........... G01N 27/221 |

(Continued)

OTHER PUBLICATIONS

M. Carminati et al., Flexible Impedance Sensor for In-Line Monitoring of Water and Beverages, May 1, 2019, IEEE International Symposium on Circuits and Systems (ISCAS), pp. 1-4 (Year: 2019).*

*Primary Examiner* — Marrit Eyassu
(74) *Attorney, Agent, or Firm* — Husch Blackwell LLP

(57) ABSTRACT

A flexible wafer probe for testing the level of dissolved solids in a water source and a method of use are provided. The probe may have an adhesive coating so that the probe may be affixed to a surface, such as the interior of a conduit. The flexibility of the probe may allow the probe to be affixed to surfaces of various shapes. The probe may have a low profile such that it does not impede water flow through the conduit. The probe may be provided in the form of a flexible, thin circular pad composed of three layers. The first and third layers may compose the outside surfaces of the probe and may render the probe waterproof. The measuring instruments of the probe may be affixed to the second layer and exposed to the water through apertures that extend through the first layer of the probe.

20 Claims, 8 Drawing Sheets

(56) References Cited

U.S. PATENT DOCUMENTS

| | | | | |
|---|---|---|---|---|
| 2011/0023586 A1* | 2/2011 | Leyer | ............... | G01D 11/245 73/53.01 |
| 2013/0182745 A1* | 7/2013 | Hertel | ............... | G01K 7/16 374/185 |

FOREIGN PATENT DOCUMENTS

| | | | | | |
|---|---|---|---|---|---|
| KR | 101685531 B1 | * | 12/2016 | | |
| KR | 20170010790 A | * | 2/2017 | | |
| WO | WO-2015038991 A1 | * | 3/2015 | ............ | G01C 23/00 |

\* cited by examiner

FLEXIBLE WAFER TOTAL DISSOLVED SOLIDS PROBE AND METHODS OF USE THEREOF

CROSS-REFERENCE TO RELATED APPLICATIONS

This application claims priority to U.S. Provisional Application No. 63/200,951 filed Apr. 5, 2021, which is incorporated by reference in its entirety for all purposes.

BACKGROUND

The term "dissolved solids" refers generally to any minerals, salts, metals, cations or anions that are dissolved in a water sample. Dissolved solids include many of the substances that impair water color, odor, taste, or overall water quality. Many industries require that the water used be held to stringent standards such that the color, odor, or taste of the water does not have any adverse effect on the end product. Many available water supplies exceed the EPA's recommended maximum total dissolved solids (TDS) level of 500 parts per million; therefore treatment and monitoring of water sources for TDS levels is important to maintaining a desired water quality for particular industrial or commercial activities.

The monitoring of TDS levels from a water source can effectively help in determining the appropriate types of water processing and/or treatment that must be applied to the water to obtain a water output within a desired range of TDS levels. Further, the measurement of TDS in a water supply is also important for the continual monitoring of the water from the purification system to ensure that the desired TDS output levels are being achieved. A detected rise in the measured TDS level may be indicative of increased contaminants in the water supply source, and a new or modified water purification system may be needed. Alternatively, the detected rise in measured TDS may be indicative of reduced filtering capacity, thus indicating that it is time to replace a filter or membrane in the water purification system.

Devices and methods currently exist for monitoring the TDS in a water source. Many of these devices are based on the principle that the conductivity of the water being tested increases as the TDS in the water increases. Therefore, the TDS may be measured by inserting a pair of electrodes into the water to be tested and measuring the conductivity between the two electrodes experienced by a current passed between them. TDS meters have been developed both as stationary in line systems that are disposed into the water purification system just prior to the water output, or may exist as a portable, handheld device.

However, many in-line and handheld TDS sensors are not practical for long-term use within a conduit or pipe. First, when using in-line TDS sensors, an o-ring is typically used to protect against fluid leakage from the conduit. If a user wishes to replace the TDS sensor, the new sensor may not be compatible with the o-ring used with the previous sensor. This may lead to additional cost and inconvenience for the user if the o-ring must be replaced. Second, if there is not a previously existing access port available for the TDS sensor within the conduit, a large channel must be cut into the conduit to accommodate the body of the sensor. Creating a channel within the conduit can be time consuming and may cause fluid leakage if the channel is not properly sealed. Third, both in-line and handheld TDS sensors can impede fluid flow through the conduit, especially in small diameter conduits. Fourth, handheld probes are inconvenient for long-term monitoring of TDS levels within a conduit since the probe must be manually inserted into the water for each TDS test. Finally, many handheld probes are not designed for long-term use, but rather are designed for single or short-term use.

SUMMARY

Some embodiments provide for a low-cost, low-profile, and flexible total dissolved solids (TDS) probe for use in aquatic environments including, but not limited to, water filtration systems. The probe is designed for long-term use within pipes or conduits in water filtration systems.

The probe may be provided in the form of a flexible body. The flexible body may be formed from a first, a second, and a third layer that are provided in the shape of thin circular pads. Each layer may be composed of a flexible material that allows the flexible body to assume a variety of shapes. Further, the flexible body may have a low profile such that the probe may not impede the water flow through the conduit. In one embodiment, to form the flexible body, a bottom surface of the first layer may be attached to a top surface of the second layer, and a bottom surface of the second layer may be attached to a top surface of the third layer. Thus, in this embodiment, the first and third layers together may provide a waterproof seal around the second layer and various measuring instruments disposed within the flexible body.

The first layer may be provided with apertures that extend through the entirety of the thickness of the circular pad. The apertures may allow for the measuring instruments located within the probe to interact with the aquatic environment so that various quantities of the water may be measured. For example, a thermistor may be used to measure the temperature of the water, and an electrode pair may be used to measure the conductivity of the water. Together, the temperature and conductivity measurements may be used to produce a TDS reading. Other measuring instruments may be incorporated into the probe to measure additional physical and chemical properties of the water.

The second layer may be a flexible printed circuit board (PCB) upon which the measuring instruments of the probe are affixed. In one embodiment, the probe includes the thermistor and the electrode pair, but other measuring instruments may also be affixed to the second layer. The flexible PCB may also have traces that are in communication with circuitry disposed outside the probe, such as a control unit and/or a microprocessor. The traces may also connect the measuring instruments to a power source. In other embodiments, some or all of the components of the outside circuitry may be located within the probe itself. In yet other embodiments, the probe may contain a battery and a wireless communication system such that the probe need not be physically connected with the outside circuitry.

A bottom surface of the third layer may be coated or affixed with an adhesive that may allow a user to attach the probe to a surface. Because the probe is provided in the form of a flexible body, the flexible body of the probe may be bent such that the curvature of the flexible body is substantially the same as the curvature of the conduit to which the probe may be affixed. By bending the flexible body, a user may affix the entire bottom surface of the third layer to the selected conduit surface. Further, the probe may seal an opening in the conduit if the probe is affixed to the conduit surface over the opening.

A method of using the probe is also provided herein. The method may include the steps of a user obtaining a probe, selecting a surface within a conduit to adhere the probe to, bending the flexible body of the probe such that the curvature of the flexible body is substantially the same as the curvature of the conduit, adhering the bottom surface of the probe to the conduit, and then using the probe to measure the TDS level of the water.

DETAILED DESCRIPTION

Figure 1:
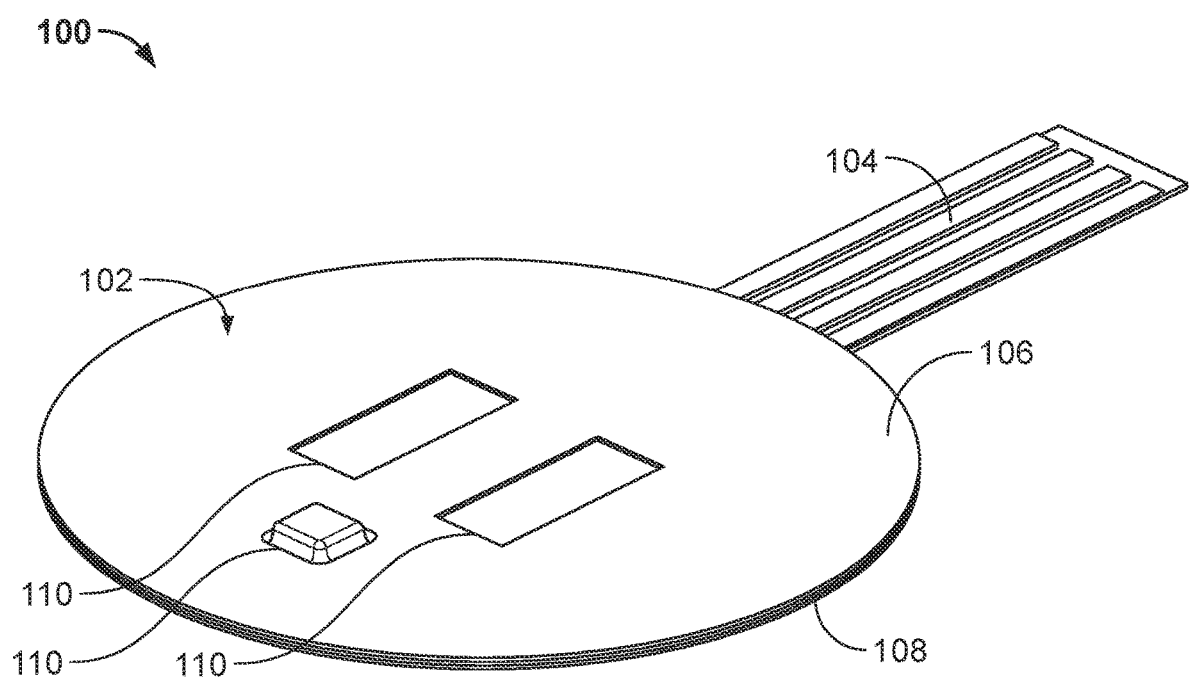
FIG. 1 is an isometric view of a flexible wafer total dissolved solids (TDS) probe according to one embodiment.

Before any embodiments are described in detail, it is to be understood that the disclosure is not limited in its application to the details of construction and the arrangement of components set forth in the following description or illustrated in the following drawings, which is limited only by the claims that follow the present disclosure. The disclosure is capable of other embodiments, and of being practiced, or of being carried out, in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following description is presented to enable a person skilled in the art to make and use embodiments of the disclosure. Various modifications to the illustrated embodiments will be readily apparent to those skilled in the art, and the generic principles herein can be applied to other embodiments and applications without departing from embodiments of the disclosure. Thus, embodiments of the disclosure are not intended to be limited to embodiments shown but are to be accorded the widest scope consistent with the principles and features disclosed herein. The following detailed description is to be read with reference to the figures, in which like elements in different figures have like reference numerals. Skilled artisans will recognize the examples provided herein have many useful alternatives and fall within the scope of embodiments of the disclosure.

Additionally, while the following discussion may describe features associated with specific devices, it is understood that additional devices and or features can be used with the described systems and methods, and that the discussed devices and features are used to provide examples of possible embodiments, without being limited.

The present disclosure is directed toward a flexible wafer total dissolved solids (TDS) probe. The flexibility of the probe may allow its shape to be adapted for placement in a wide variety of aquatic environments including, but not limited to, variously shaped and sized conduits within water filtration systems and other aquatic systems. The low profile of the probe may ensure that it does not impede the flow of water through the conduits. Also, the probe may have an adhesive such that it can be adhered to the surface of the conduit in which it is placed.

The probe may measure physical quantities of the water including, but not limited to, the TDS level and temperature of the water. Other embodiments of the probe may also measure chemical properties of the water, e.g. pH. Measuring TDS levels may assist a user in determining the type of water purification system needed to treat the water. Measuring TDS levels may also assist the user in the continual monitoring of the water from a water purification system to ensure that the desired TDS output levels are being achieved. Further, multiple probes may be used within a water filtration system to monitor the system's input and output TDS levels. This information may assist a user in determining whether the water filtration system is functioning properly or whether a membrane or filter within the filtration system should be replaced.

FIG. 1 illustrates a probe 100, which may be provided in the form of a flexible body 102 and wires 104 protruding outwardly therefrom. The flexible body 102 may be provided in the form of a flexible circular pad with a top surface 106 and a bottom surface 108. The flexible body 102 defines an interior compartment that is designed to substantially enclose one or more measuring instruments of the probe 100 that are designed to measure one or more water quality parameters, such as, for example, TDS and temperature measurements. The flexible body 102 may be provided as a waterproof, flexible material including, but not limited to, vinyl. The waterproof nature of the flexible body 102 may protect the measuring instruments located within the interior of the flexible body 102. The flexibility of the body 102 of the probe 100 is designed to allow its shape to be adapted to conform to the shape of a surface (e.g., a pipe or conduit) the probe 100 may be affixed to.

The top surface 106 of the flexible body 102 may have at least one aperture 110 provided therein. As depicted in FIG. 1, there may be three apertures 110. The apertures 110 may be disposed in the center of the flexible body 102 and extend through the thickness of the top surface 106. The apertures 110 may allow the measuring instruments of the probe 100 to be exposed the aquatic environment such that properties of the water may be measured by the probe 100.

The bottom surface 108 of the flexible body 102 may have an adhesive backing that may allow the probe 100 to be affixed to a surface, e.g. the surface of a water pipe. The adhesive may be selected to be compatible with the surface that the probe 100 will be affixed to.

The wires 104 provide electrical communication between the measuring instruments of the probe 100 contained within the flexible body 102 and outside circuitry (not illustrated) disposed outside of the probe 100. The outside circuitry may include, but is not limited to, a power source, a control unit, a microprocessor, a computer, a network, and a user device such as a smart phone, etc. (not shown). The wires 104 may be composed of long thin strands of copper, or other conductive metals known to those in the art. The wires 104 may terminate at the probe 100 and at the outside circuitry. In various embodiments, the wires 104 and the outside circuitry may serve a variety of functions. First, the wires 104 may supply electricity to the probe 100 from the power source. Second, the wires 104 may allow for one-way or two-way communication between the probe 100 and the outside circuitry. Third, the control unit, via the wires 104, may direct the probe 100 to measure the TDS level and/or temperature of the water. Fourth, the outside circuitry, including the microprocessor, may interpret signals produced by the probe 100 to determine the TDS level. Fifth, the outside circuitry may include a display to relay information obtained by the probe 100 directly to the user or the outside circuitry may transmit the information to a centralized data collection processor. In other embodiments, some or all of the components of the outside circuitry may be contained within the body of the probe 100. In yet other embodiments, the probe 100 may be equipped with a wireless communication system such that the probe 100 may wirelessly communicate with the outside circuitry.

Figure 2:
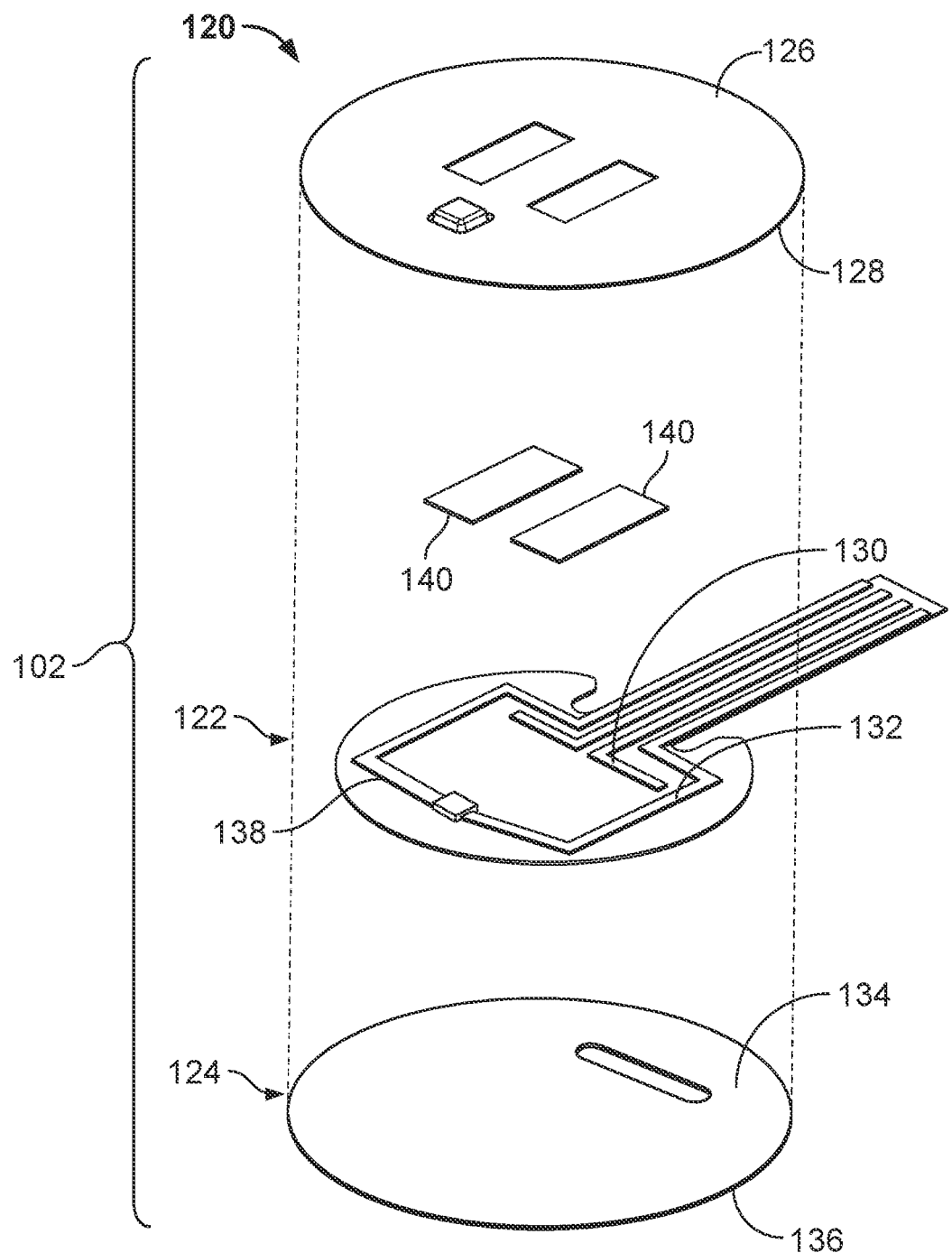
FIG. 2 is an exploded view of an embodiment of the flexible wafer TDS probe of FIG. 1.

FIG. 2 illustrates an embodiment of an exploded view of the probe 100. In this embodiment, the flexible body 102 of the probe 100 is constructed of a first layer 120, a second layer 122, and a third layer 124. The layers 120, 122, and 124 may be substantially the same size and formed in the shape of a circular pad with thin sidewalls. Each of the layers 120, 122, and 124 may be composed of a flexible material including, but not limited to, vinyl. The flexibility of the layers 120, 122, and 124 may allow for the shape of the probe 100 to be adapted to conform to the shape of the surface the probe 100 may be affixed to. In other embodiments, instead of being constructed of three layers, the probe 100 may be constructed of at least two layers or molded as one piece, as would be appreciated by those skilled in the art. In the embodiments where the probe 100 may be molded as one piece, the probe 100 may include an interior cavity in which the measuring instruments of the probe may be disposed.

The first layer 120 has a top surface 126 and a bottom surface 128, the second layer 122 has a top surface 130 and a bottom surface 132, and the third layer 124 has a top surface 134 and a bottom surface 136. To form the flexible body 102, the bottom surface 128 of the first layer 120 may be attached to the top surface 130 of the second layer 122, and the bottom surface 132 of the second layer 122 may be attached to the top surface 134 of the third layer 124. In this arrangement, only the top surface 126 and the bottom surface 136 may be exposed to the aquatic environment, protecting the second layer 122 and the measuring instruments disposed within the flexible body 102 from the aquatic environment by forming a substantially water-proof/water tight seal.

The second layer 122 is provided with a flexible printed circuit board (PCB) 138 upon which metallic strips 140 may be affixed. The flexible PCB 138 may be composed of a flexible dielectric material, such as polyimide, as would be appreciated by those in the art. The measuring instruments that may carry out the temperature and TDS level measurements may be affixed to the PCB 138.

Figure 3:
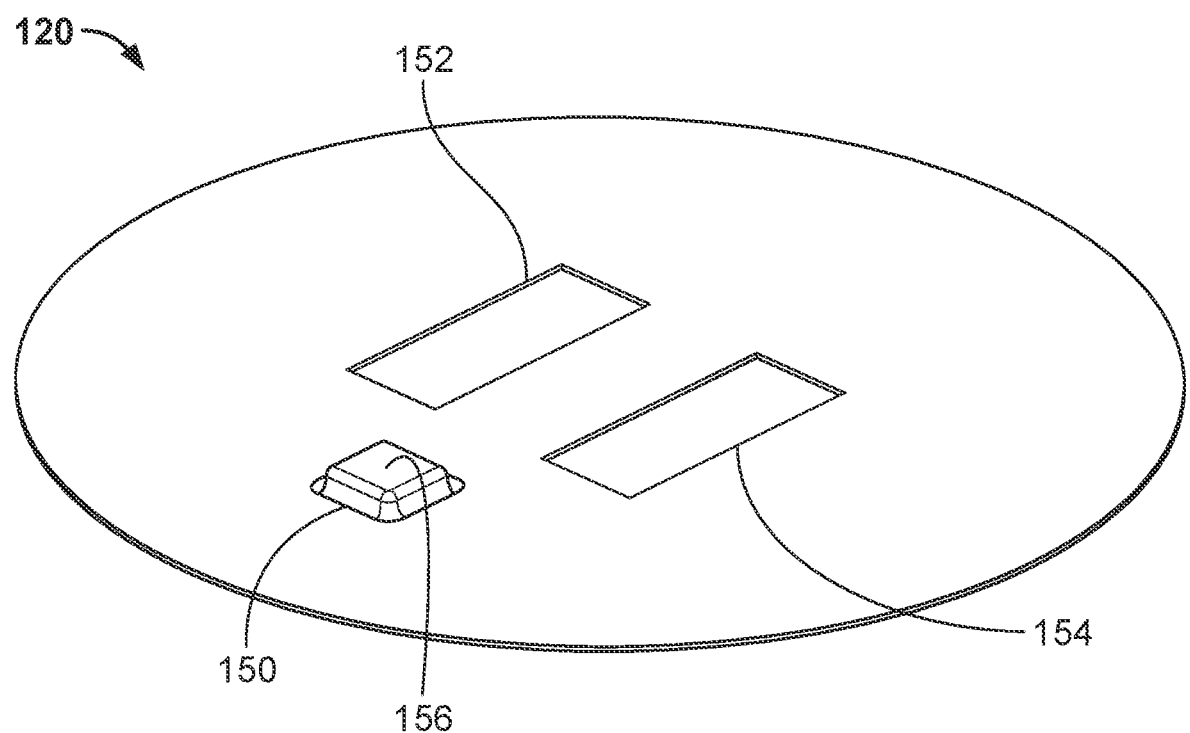
FIG. 3 is an isometric view of a first layer of the flexible wafer TDS probe of FIG. 1.

FIG. 3 illustrates an embodiment of the first layer 120 of the probe 100, the first layer having apertures 150, 152, 154 and a thermistor cover 156. Generally, the first layer 120 may be provided in the form of a flexible circular pad having at least one aperture. The at least one aperture may extend through the thickness of the circular pad and be disposed of within a center portion of the circular pad. In the embodiment illustrated in FIG. 3, the first layer 120 has apertures 150, 152, and 154 that are sized to accommodate the measuring instruments housed in the flexible body 102. The apertures 150, 152, and 154 may expose one or more portions of the measuring instruments to the aquatic environment, as described herein.

The thermistor cover 156 may extend upwardly through the aperture 150. The thermistor cover 156 may be composed of a heat-conductive, waterproof material and may be formed in the shape of a rectangular prism. The bottom portion (not illustrated) of the thermistor cover 156 may be substantially the same size as the aperture 150 to ensure water does not enter the flexible body 102. When the first layer 120 is attached to the second layer 122, the thermistor cover 156 is designed to enclose a thermistor 160 that can measure the temperature of the aquatic environment.

Figure 4:
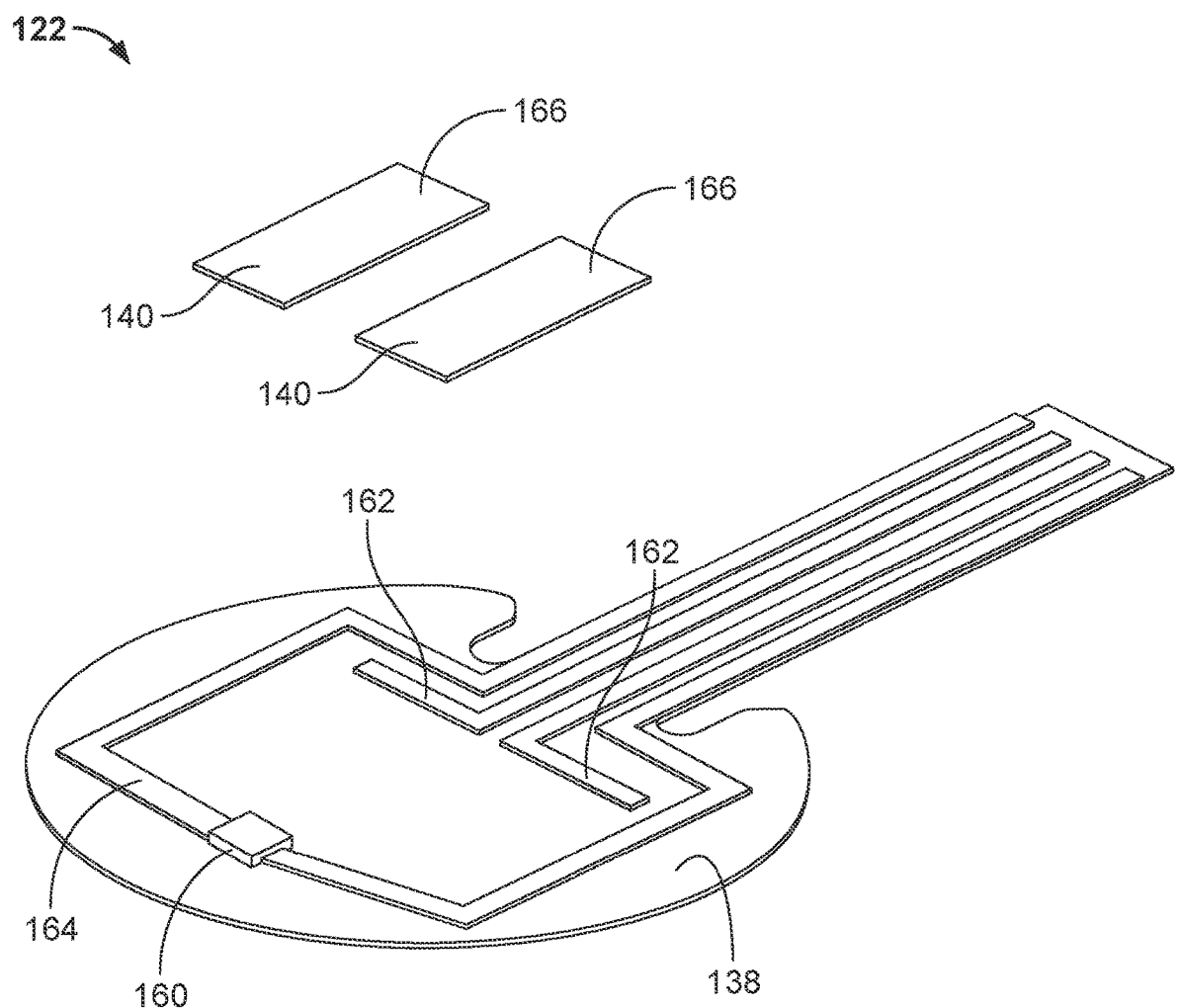
FIG. 4 is an isometric view of a second layer of the flexible wafer TDS probe of FIG. 1.

FIG. 4 illustrates an embodiment of the second layer 122 of the probe 100. The second layer 122 may be composed of the flexible PCB 138 upon which the thermistor 160, the metallic strips 140, metallic attachments 162, and traces 164 are affixed. In other embodiments, the second layer 122 may be provided with additional measuring instruments that may measure additional properties of the aquatic environment.

The thermistor 160 is designed to measure the temperature of the aquatic environment. The thermistor 160 may be provided in the form of a thin rectangular prism, though other shapes are foreseeable. The thermistor 160 is in electrical communication with the traces 164. The thermistor 160 may be substantially the same size as the opening at the bottom of the thermistor cover 156 (not illustrated). As known in the art, a thermistor (as provided in FIGS. 2, 4, and 6) is a resistor whose resistance is temperature dependent. Thus, when a constant current is supplied to the thermistor, a change in the voltage across the thermistor indicates a change in temperature. Specific voltages across the thermistor may be correlated with specific temperatures such that a microprocessor can convert the measured voltage across the thermistor into a temperature output. Measuring the water temperature may assist the probe 100 in producing accurate TDS readings.

The metallic strips 140 may be provided in the form of a corrosion resistant metal including, but not limited to, stainless steel. The metallic strips 140 may be provided in the form of thin rectangular prisms. Top surfaces 166 of the metallic strips 140 may be substantially the same size as, or slightly larger than, the openings provided by the apertures 152 and 154 (illustrated in FIG. 3). The metallic strips 140 may be connected to the wires 104 via the metallic attachments 162. The metallic strips 140 (as provided in FIGS. 1, 2 and 4) may act as an electrode pair that are designed to measure the conductivity of the water.

To measure the water's conductivity, voltage may be applied to the metallic strips 140. The voltage drop across the metallic strips 140 is due to the resistance of the water and may be used to calculate the conductivity of the water. Because the water's conductivity is directly related to the TDS concentration of the water, the conductivity measurement may be converted into a TDS level. In addition, the measured TDS level may be calibrated to account for the water temperature (as measured by the thermistor 160) to produce a more accurate TDS reading. Finally, after a TDS level is obtained, the polarity of the metallic strips 140 may be reversed to reduce any scaling or deposit buildup that may form on the metallic strips 140 during conductivity testing. Reducing scaling or deposit buildup on the metallic strips 140 may prolong the life of the probe 100.

The metallic strips 140 may be connected to the wires 104 via the metallic attachments 162. Thus, the metallic attachments 162 form an electrical circuit that may allow for electricity to flow to and from the metallic strips 140. The metallic attachments 162 may be thin metallic strips that are attached to the wires 104. Alternatively, the metallic attachments 162 may be formed in one piece with the wires 104. The metallic attachments 162 may be bi-metallic to prevent galvanic corrosion as the probe 100 measures the TDS level of the water.

The traces 164 may be provided in the form of electrically conductive thin metal strips. The traces 164 may be disposed of in the center or along the outside edge of the second layer 122. The traces 164 provide electrical communication between the measuring instruments affixed to the flexible PCB 138 and the wires 104. The traces 164 may allow electricity to be supplied to the measuring instruments via the wires 104 and may allow for one-way or two-way communication between the measuring instruments and the outside circuitry (not illustrated). In the embodiment illustrated in FIG. 4, the traces 164 connect the thermistor 160 to the outside circuitry via the wires 104.

Figure 5:
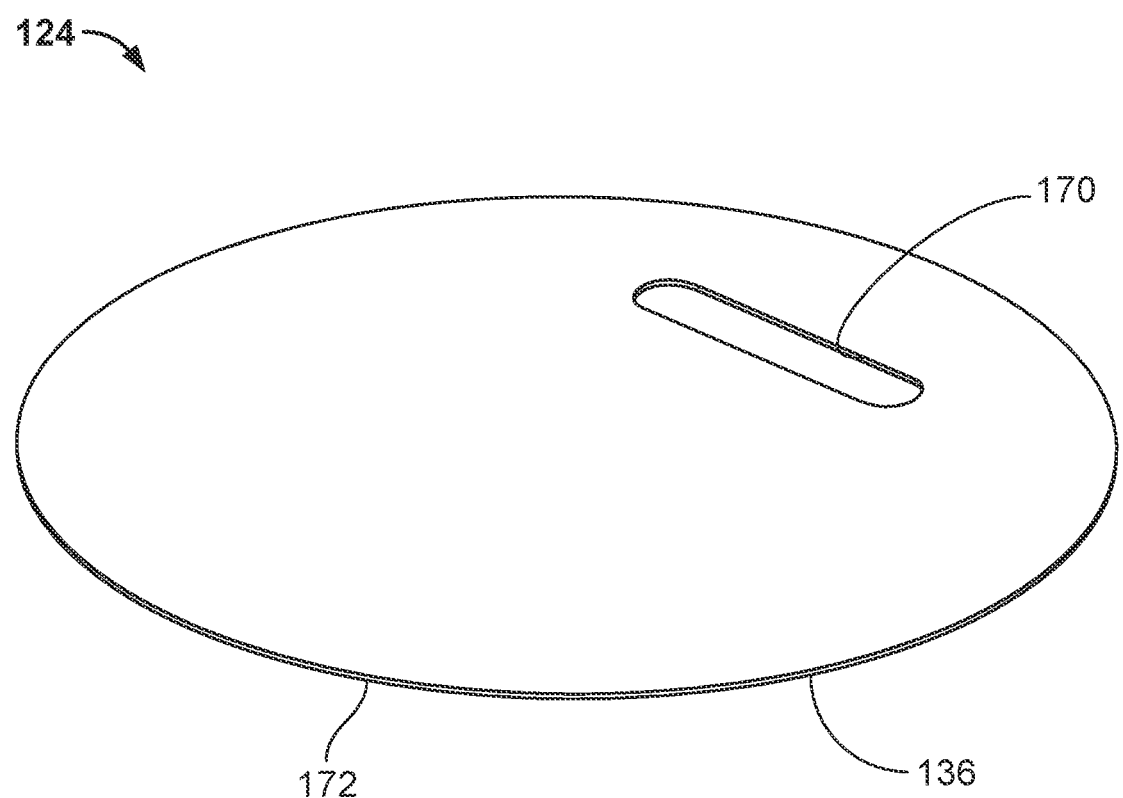
FIG. 5 is an isometric view of a third layer of the flexible wafer TDS probe of FIG. 1.

FIG. 5 illustrates an embodiment of the third layer 124 having the bottom surface 136 and an aperture 170. Generally, the third layer 124 may be provided in the form of a flexible circular pad having at least one aperture. The at least one aperture may extend through the entirety of the thickness of the circular pad and be disposed of within a center portion of the circular pad. In the embodiment illustrated in FIG. 5, the third layer 124 has the aperture 170 through which the wires 104 may be inserted. The size and shape of the aperture 170 is provided to correspond to the size and shape of the wires 104 to allow for the wires 104 to extend through the aperture 170 and help the probe 100 remain waterproof.

In some embodiments, the bottom surface 136 of the third layer 124 may be coated or equipped with an adhesive 172. The adhesive 172 may allow for the bottom surface 136 to be affixed to a surface including, but not limited to, the surface of a pipe. The adhesive 172 may be selected from adhesives known in the art such that the adhesive is compatible with the material the surface is composed of (e.g. PVC or copper). In other embodiments, the bottom surface 136 may not have an adhesive, but rather the adhesive may be directly placed onto the pipe surface before the bottom surface 136 is affixed to the pipe surface.

Figure 6:
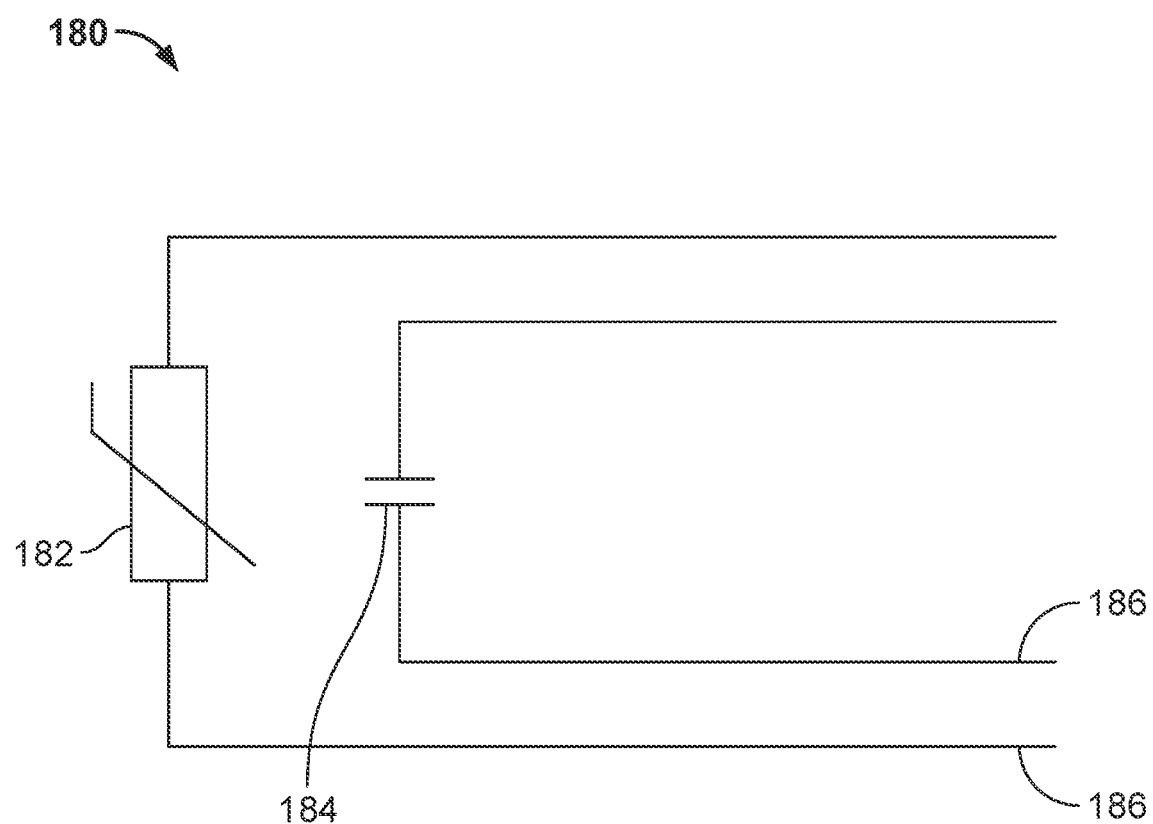
FIG. 6 is a schematic diagram of an electrical circuit of the flexible wafer TDS probe of FIG. 1.

FIG. 6 illustrates a schematic diagram of an embodiment of the probe 100. The schematic diagram illustrates an electrical circuit 180 having a thermistor 182, an electrode pair 184, and wires 186. In other embodiments, additional components may be added to the electrical circuit 180. The electrical circuit 180 may be disposed within the flexible body 102 of the probe 100. In one embodiment, the electrical circuit 180 is disposed on the flexible PCB 138 of the second layer 122.

The thermistor 182, the electrode pair 184, and the wires 186 illustrated in FIG. 6 correspond to the thermistor 160, the metallic strips 140, and the traces 164 illustrated in previous figures. In FIG. 6, the thermistor 182 and the electrode pair 184 may be connected to outside circuitry (not illustrated) via the wires 186. As explained previously, the thermistor 182 may measure the water's temperature and the electrode pair 184 may measure the water's conductivity.

Figure 7:
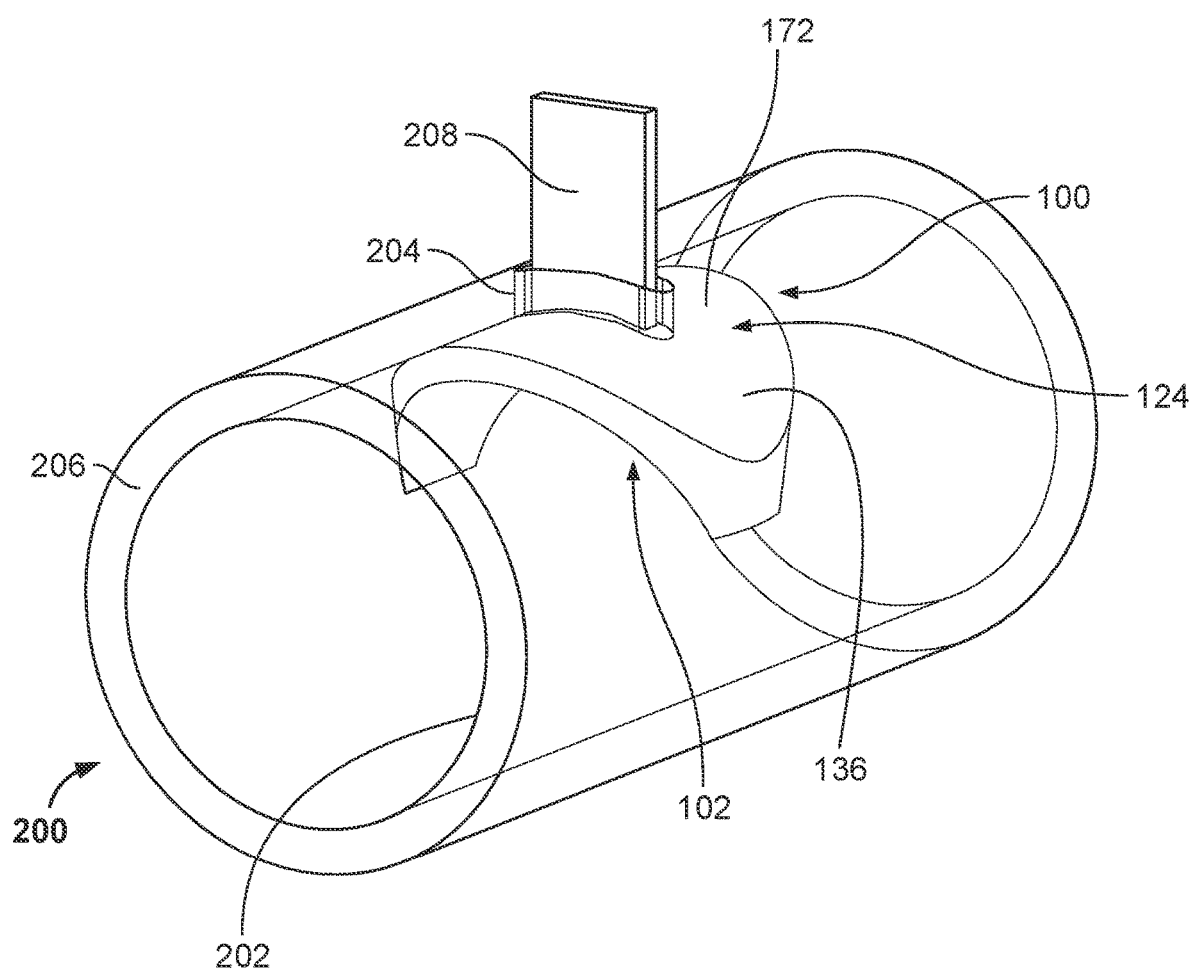
FIG. 7 is an isometric view of an embodiment of the flexible wafer TDS probe of FIG. 1 disposed within a representative pipe in an in-use configuration.

FIG. 7 illustrates the probe 100 affixed to a representative pipe 200. The pipe 200 is defined by a conduit having a wall 206 with an interior surface 202.

The adhesive 172 on the bottom surface 136 may allow for the probe 100 to be affixed to the pipe 200 for long-term use. The flexibility of the flexible body 102 may allow the shape of the probe 100 to be adapted to be substantially the same shape as a surface that the probe 100 is affixed to. For example, in FIG. 7, the flexible body 102 has substantially the same curvature as the interior surface 202 of the pipe 200, which may allow the bottom surface 136 of the third layer 124 to abut the interior surface 202.

In addition, the flexible body 102 is designed to have a low profile (e.g., relatively small total thickness) such that the probe 100 may not substantially interfere with the flow of water through the pipe 200.

In the embodiment illustrated in FIG. 7, the pipe 200 further includes a channel 204 that extends upwardly through the wall 206 of the pipe 200. The insulated wires 208, which may contain the wires 104 (not illustrated), may extend from the probe 100 and through the channel 204. The channel 204 may have substantially the same shape and size dimensions as the insulated wires 208 to help prevent water leakage from the pipe 200. Also, the bottom surface 136 of the third layer 124 of the probe 100, in conjunction with the adhesive 172, may seal the channel 204 such that water will not leak out of the pipe 200 through the channel 204. In effect, this may allow for the probe 100 to be self-sealing when it is affixed over a channel such as the channel 204.

In other embodiments, the probe 100 may wirelessly communicate with the outside circuitry (not illustrated) such that the insulated wires 208 are unnecessary. If insulated wires are not used as part of the probe 100, a channel need not be created in the pipe 200.

Figure 8:
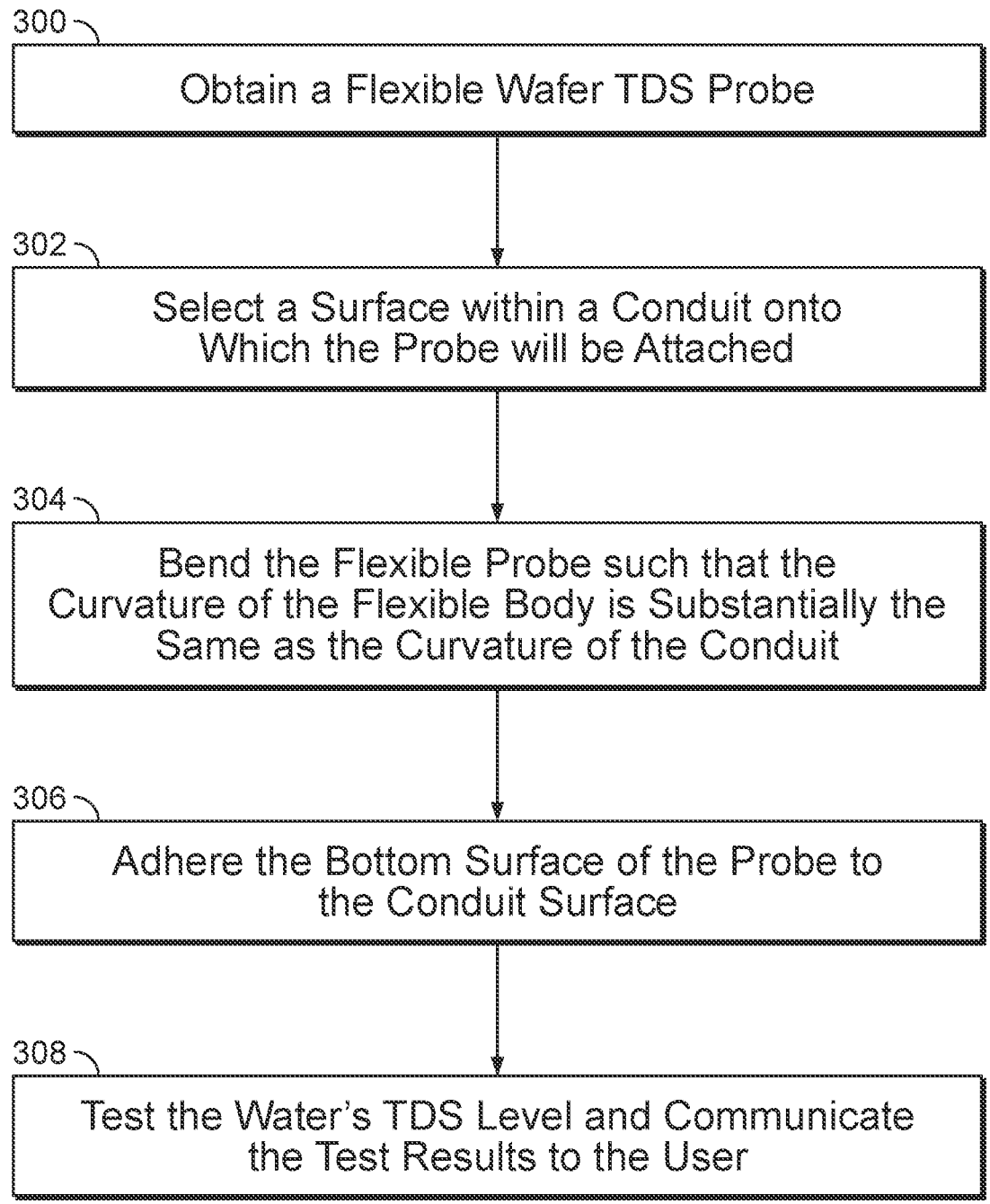
FIG. 8 is a schematic representation of a method of using the flexible wafer TDS probe of FIG. 1.

FIG. 8 depicts a flow chart illustrating the steps of one embodiment of a method for using the probe 100 to measure TDS levels. First, a user may obtain a flexible wafer TDS probe at step 300. The flexible wafer TDS probe may be obtained through various channels. Second, at step 302, the user may select an appropriate surface within a conduit onto which the probe will be attached. The surface is preferably compatible with the adhesive 172 such that the probe may adhere to the selected surface. Third, at step 304, the user may bend the flexible probe so that the curvature of the flexible body is substantially the same as the curvature of the conduit. Fourth, at step 306, the user may adhere the bottom surface of the probe to the conduit surface. Finally, at step 308, the probe may measure the TDS level of the water and communicate the results to the consumer. The TDS level may be displayed on a screen or may be stored for later reference. Step 308 may be repeated as many times as a user or technician wishes to measure the TDS level of the water at a time interval or frequency desired by a user.

It will be appreciated by those skilled in the art that while the above disclosure has been described above in connection with particular embodiments and examples, the above disclosure is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the above disclosure are set forth in the following claims.

The invention claimed is:

1. A probe comprising:
   a flexible body including:
      a top surface and a bottom surface;
      a first aperture disposed within the top surface;
      an adhesive disposed on the bottom surface; and
      a thermistor disposed within the flexible body and extending at least partially into the first aperture, wherein the probe is adapted to measure a level of total dissolved solids in an aquatic environment.

2. The probe of claim 1, wherein the flexible body is substantially flat when the probe is in a first configuration, and the flexible body is shaped to substantially match a curvature of a surface within the aquatic environment when the probe is in a second configuration.

3. The probe of claim 1 further including:
a pair of electrodes designed to measure a conductivity of the aquatic environment; and
a second aperture and a third aperture each disposed within the top surface of the probe;
wherein a first electrode of the pair of electrodes is positioned and located proximate to the second aperture and a second electrode of the pair of electrodes is positioned and located proximate to the third aperture.

4. The probe of claim 3, wherein a first measured value is determined by at least the pair of electrodes, a second measured value is determined by at least the thermistor, and wherein the level of total dissolved solids within the aquatic environment is determined using at least the first measured value and the second measured value.

5. The probe of claim 1 further including a thermistor cover extending through the first aperture, the thermistor cover designed to enclose the thermistor.

6. The probe of claim 1 further including at least one wire electrically coupled to the thermistor, wherein the at least one wire extends through the bottom surface of the flexible body.

7. The probe of claim 1, wherein the flexible body further includes:
a first layer including an upper surface and a lower surface positioned opposite the upper surface, the first layer including the first aperture;
a second layer including an upper surface and a lower surface positioned opposite the upper surface, the second layer disposed adjacent to the lower surface of the first layer, the second layer including a printed circuit board; and
a third layer including an upper surface and a lower surface positioned opposite the upper surface, the third layer disposed adjacent to the lower surface of the second layer, wherein the third layer includes at least one aperture extending through the third layer, and is adapted to adhere to a surface contained within the aquatic environment;
wherein the printed circuit board is electrically coupled to an electrode pair and the thermistor and the at least one aperture is adapted to place each electrode of the electrode pair in fluid communication with the aquatic environment,
wherein the first layer provides the top surface of the flexible body, the third layer provides the bottom surface of the flexible body, and the second layer is positioned between the first layer and the third layer.

8. The probe of claim 7, wherein the third layer is adapted to seal a channel of a pipe from the aquatic environment.

9. The probe of claim 7, wherein a polarity of each electrode of the electrode pair is reversed after a conductivity of the fluid of the aquatic environment is measured.

10. The probe of claim 7, wherein each electrode of the electrode pair is coupled to the printed circuit board by a bi-metallic attachment.

11. The probe of claim 7 further including one or more wires extending through the at least one aperture of the third layer of the flexible body, the one or more wires adapted to provide power to the probe and to establish communication between the probe and an outside circuitry.

12. The probe of claim 7, wherein the printed circuit board is provided as a flexible printed circuit board.

13. The probe of claim 1 further including a microprocessor designed to interpret signals generated by the thermistor.

14. The probe of claim 1, wherein:
at least one measuring instrument is coupled to the flexible body, the at least one measuring instrument designed to measure at least one property of the aquatic environment, and
an external system located remote from the probe is in wireless communication with the probe.

15. The probe of claim 14, wherein:
the at least one measuring instrument includes at least one of the thermistor, an electrode pair, or a pH sensor; and
the at least one property is at least one of a physical or a chemical property.

16. The probe of claim 14, wherein the external system includes a display adapted to convey information obtained by the probe to a user.

17. The probe of claim 14, wherein the probe and the external system are in two-way communication with one another.

18. The probe of claim 14, wherein the external system transmits information from the probe to a centralized data collection processor.

19. The probe of claim 14, wherein the external system includes at least one of a control unit, a microprocessor, a computer, a network, or a smart phone.

20. The probe of claim 14, wherein the external system is adapted to direct the probe to measure the level of total dissolved solids within the aquatic environment.

* * * * *